(12) United States Patent
Parkar et al.

(10) Patent No.: US 12,257,092 B2
(45) Date of Patent: Mar. 25, 2025

(54) METHOD TO SUPERIMPOSE RENDERING OVER SPINE HARDWARE IMPLANTS ON IMAGES PRODUCED BY CBCT SCANNER SYSTEM

(71) Applicant: Medtronic Navigation, Inc., Louisville, CO (US)

(72) Inventors: Rasika A. Parkar, Wayland, MA (US); Michael P. Marrama, Ayer, MA (US); Rejeesh Radhakrishnan, Leominster, MA (US); Edward B. Lipes, Fort Collins, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 228 days.

(21) Appl. No.: 17/967,491

(22) Filed: Oct. 17, 2022

(65) Prior Publication Data

US 2024/0122562 A1 Apr. 18, 2024

(51) Int. Cl.
| | |
|---|---|
| *G06T 15/00* | (2011.01) |
| *A61B 6/03* | (2006.01) |
| *A61B 6/46* | (2024.01) |
| *G06T 19/20* | (2011.01) |

(52) U.S. Cl.
CPC .............. *A61B 6/465* (2013.01); *A61B 6/032* (2013.01); *A61B 6/463* (2013.01); *A61B 6/466* (2013.01); *G06T 15/00* (2013.01); *G06T 19/20* (2013.01); *G06T 2200/04* (2013.01); *G06T 2200/24* (2013.01); *G06T 2210/41* (2013.01); *G06T 2211/40* (2013.01); *G06T 2219/2004* (2013.01)

(58) Field of Classification Search
None
See application file for complete search history.

(56) References Cited

U.S. PATENT DOCUMENTS

| | | | |
|---|---|---|---|
| 8,320,902 B2 | 11/2012 | Moring et al. | |
| 8,320,992 B2 | 11/2012 | Frenkel et al. | |
| 8,891,847 B2* | 11/2014 | Helm | ...................... G06T 19/20 |
| | | | 382/131 |
| 10,191,615 B2 | 1/2019 | Helm et al. | |

(Continued)

FOREIGN PATENT DOCUMENTS

| | | |
|---|---|---|
| WO | 2016037160 A2 | 3/2016 |
| WO | 2020121270 A1 | 6/2020 |
| WO | 2021175644 A1 | 9/2021 |

*Primary Examiner* — Nurun Flora
(74) *Attorney, Agent, or Firm* — Harness, Dickey & Pierce, P.L.C.

(57) ABSTRACT

A method and system for identifying an implant in an x-ray image of an anatomy shown on a display screen. The method includes: displaying the image including an artifact of the implant; prompting a user to enter parameters of the implant; displaying a rendering of the implant over the image; prompting the user to position the rendering on the artifact at an accurate position corresponding to an actual position of the implant; alerting the user when the rendering is at an inaccurate position; prompting the user to reposition the rendering from the inaccurate position to the accurate position; alerting the user when the rendering is maneuvered by the user to the accurate position; and after the rendering has been maneuvered to the accurate position by the user, reconstructing the x-ray image to replace the artifact with the rendering affixed in the accurate position.

15 Claims, 9 Drawing Sheets

(56) References Cited

U.S. PATENT DOCUMENTS

| | | |
|---|---|---|
| 10,675,094 B2 | 6/2020 | Crawford et al. |
| 11,094,061 B1 * | 8/2021 | Min .................. G06F 18/10 |
| 11,135,015 B2 | 10/2021 | Crawford et al. |
| 2013/0172731 A1 | 7/2013 | Gole |
| 2020/0305979 A1 | 10/2020 | Crawford et al. |
| 2021/0045816 A1 | 2/2021 | Geist |
| 2021/0174502 A1 | 6/2021 | Slewerdsen et al. |
| 2021/0177517 A1 * | 6/2021 | Uhde .................. A61B 34/10 |
| 2022/0265320 A1 * | 8/2022 | Rout .................. A61B 17/7011 |

* cited by examiner

METHOD TO SUPERIMPOSE RENDERING OVER SPINE HARDWARE IMPLANTS ON IMAGES PRODUCED BY CBCT SCANNER SYSTEM

FIELD

The present disclosure relates to methods and systems for superimposing renderings over spine hardware implants in x-ray images.

BACKGROUND

This section provides background information related to the present disclosure, which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two-dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

The present teachings provide for a method for identifying an implant in an x-ray image of an anatomy shown on a display screen. The method includes: receiving, in a processing system, the x-ray image of the anatomy based on computed tomography (CT) projections of the anatomy; displaying the x-ray image of the anatomy on the display screen, the x-ray image including an artifact of the implant; prompting a user to enter parameters of the implant into the processing system by way of a user interface; displaying a rendering of the implant on the display screen along with the x-ray image, the rendering sized and shaped to correspond to the implant; prompting the user to position the rendering of the implant on the artifact at an accurate position corresponding to an actual position of the implant in the anatomy; alerting the user when the rendering is maneuvered by the user to an inaccurate position that is outside of a predetermined distance from the accurate position; prompting the user to reposition the rendering from the inaccurate position to the accurate position; alerting the user when the rendering is maneuvered by the user to the accurate position, or to within the predetermined distance of the accurate position; and after the rendering has been maneuvered to the accurate position by the user, reconstructing the x-ray image to replace the artifact with the rendering affixed in the accurate position.

The present teachings further provide for an image processing system for identifying an implant in an x-ray image of an anatomy shown on a display screen. The system includes a computer processor having memory storage and an image processing software module, an implant database accessible by the processor, a display, and an input device. The processor is configured to: prompt a user to enter parameters of the implant into the processor by way of the input device; display a rendering of the implant on the display along with the image, the rendering sized and shaped to correspond to the implant; prompt the user to position the rendering of the implant on the artifact at an accurate position corresponding to an actual position of the implant in the anatomy; alert the user when the rendering is maneuvered by the user to an inaccurate position that is outside of a predetermined distance from the accurate position; prompt the user to reposition the rendering from the inaccurate position to the accurate position; alert the user when the rendering is maneuvered by the user to the accurate position, or to within the predetermined distance of the accurate position; and reconstruct the image to replace the artifact with the rendering affixed in the accurate position after the rendering has been maneuvered to the accurate position by the user.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
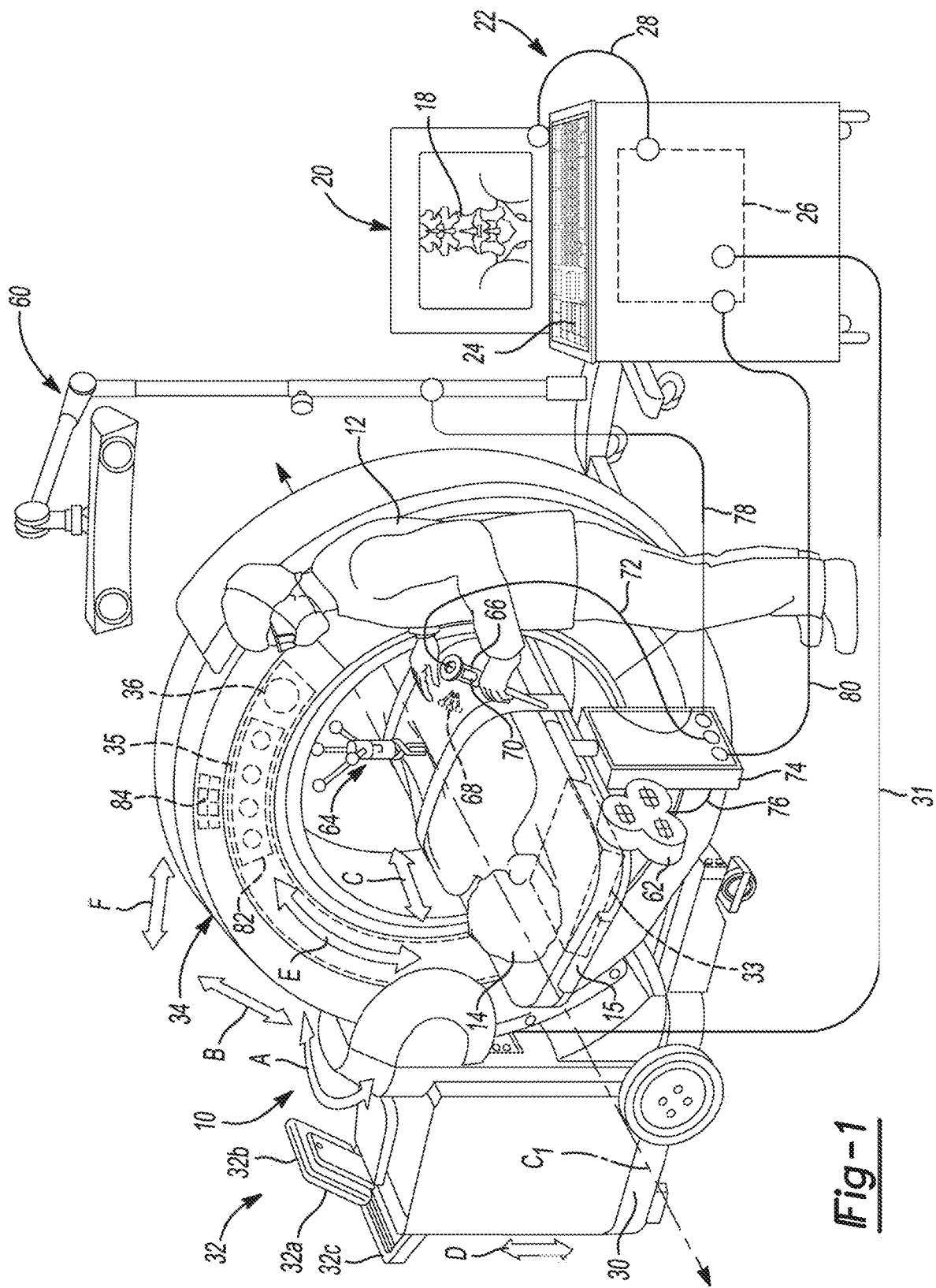
FIG. 1 is an environmental view of an exemplary imaging system.

The following description is merely exemplary in nature. It should be understood that throughout the drawings, corresponding reference numerals indicate like or corresponding parts and features. As indicated above, the present teachings are directed toward an imaging system, such as an O-Arm® imaging system commercially available from Medtronic Navigation, Inc., Louisville, CO, USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

The present teachings include the disclosure of U.S. Pat. No. 8,891,847 issued on Nov. 18, 2014 and assigned to Medtronic Navigation, Inc. of Louisville, CO, which is incorporated herein by reference. The present teachings are directed to a method of correcting artifacts caused by hardware, such as screws or other implants, in portions of the anatomy of a subject undergoing imaging by scanning methods using x-ray sources. Such implants tend to obscure the underlying anatomy of reconstructed three-dimensional (3D) images and make critical assessment of a condition (such as a defect or other pathology) or delivered therapy, including evaluating the positioning of implants, difficult.

Artifacts from implants pose a problem, for example, in x-ray computed tomography (CT), including cone beam CT (CBCT) and in other imaging methods using an x-ray source. Artifacts from implants arise because the attenuation coefficient of materials used for implants, such as, for example, metals, metal alloys, ceramics, etc., is higher than the attenuation coefficient of bones and soft tissue in the range of x-ray intensities used in such CT imaging. Flat panel detectors used to capture the images can also cause scatter that leads to artifacts at implant locations. Various methods of metal artifact reduction rely on computationally complex algorithms to remove the artifacts, use interpolation methods to fill the gaps, and re-projection of the images during 3D image reconstruction. Such methods are often difficult to implement in the operating/diagnostic imaging environment.

The present teachings provide a method for identifying an implant associated with an artifact in one or more CT slices (axial planar sections of the 3D image) after the 3D image reconstruction from a comparison database using a best fit and/or reliability method. After the best fit implant is selected from the database, an image of the selected implant is overlaid on the corresponding artifact. This correction is done after processing of the CT images for 3D reconstruction. The correction is performed on the reconstructed CT slices as a post-processing operation. In other words, processing of the images is separated from the intraoperative or real-time diagnostic scanning procedure, although it can be done in the same computer/processor used in the imaging system 10 immediately after scanning or in a different computer/processor at a later time.

Figure 2:
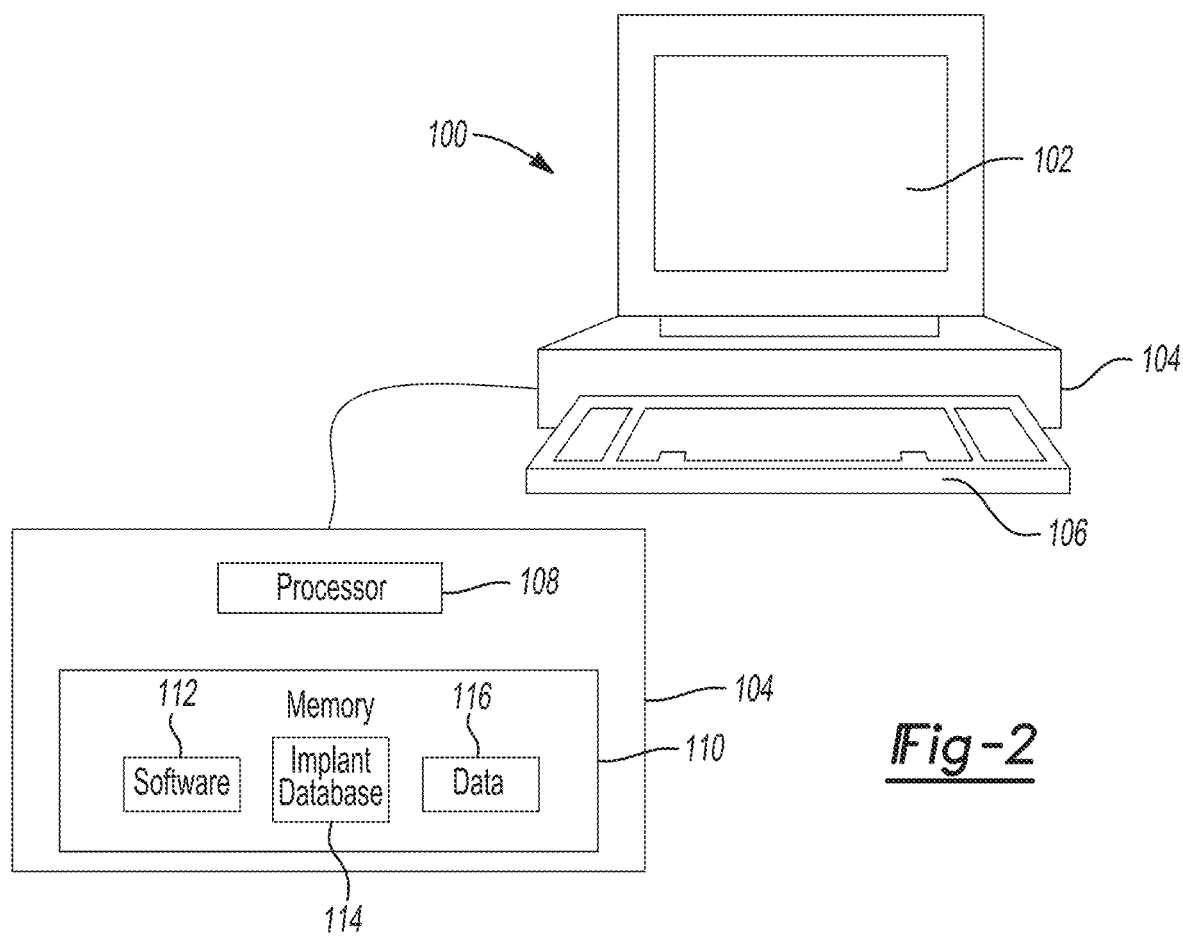
FIG. 2 is an exemplary computer system in use with the imaging system of FIG. 1.
Figure 3:
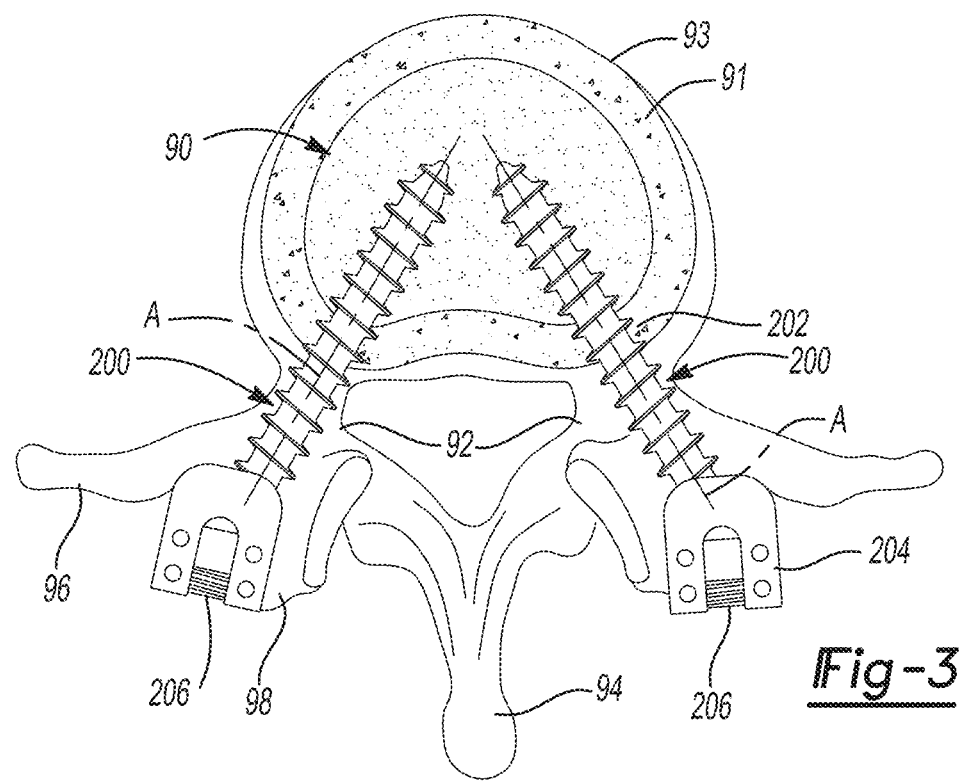
FIG. 3 is an environmental view of exemplary pedicle screws.
Figure 4:
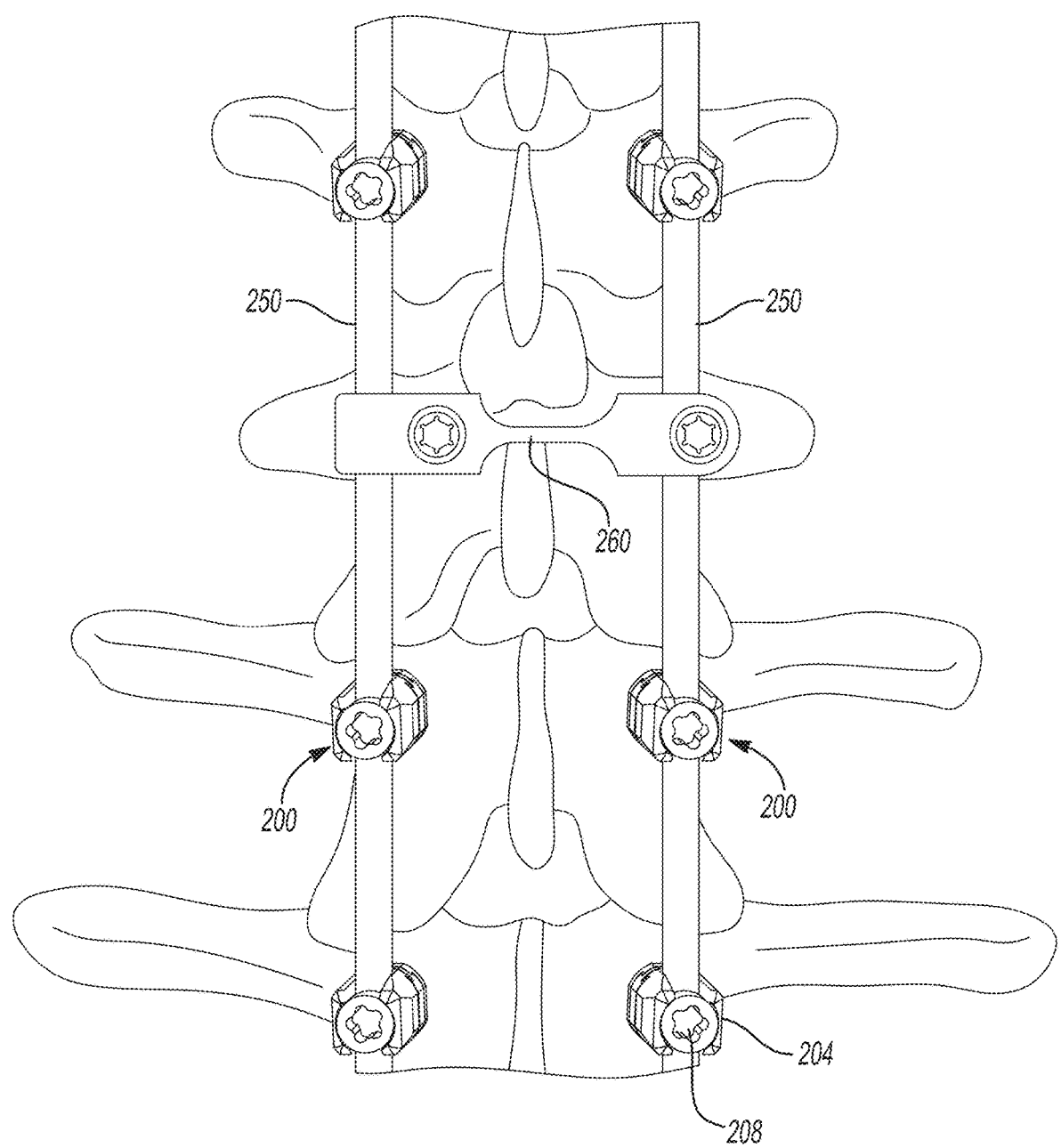
FIG. 4 is an environmental view of an exemplary spinal fixation implant including pedicle screws.
Figure 6:
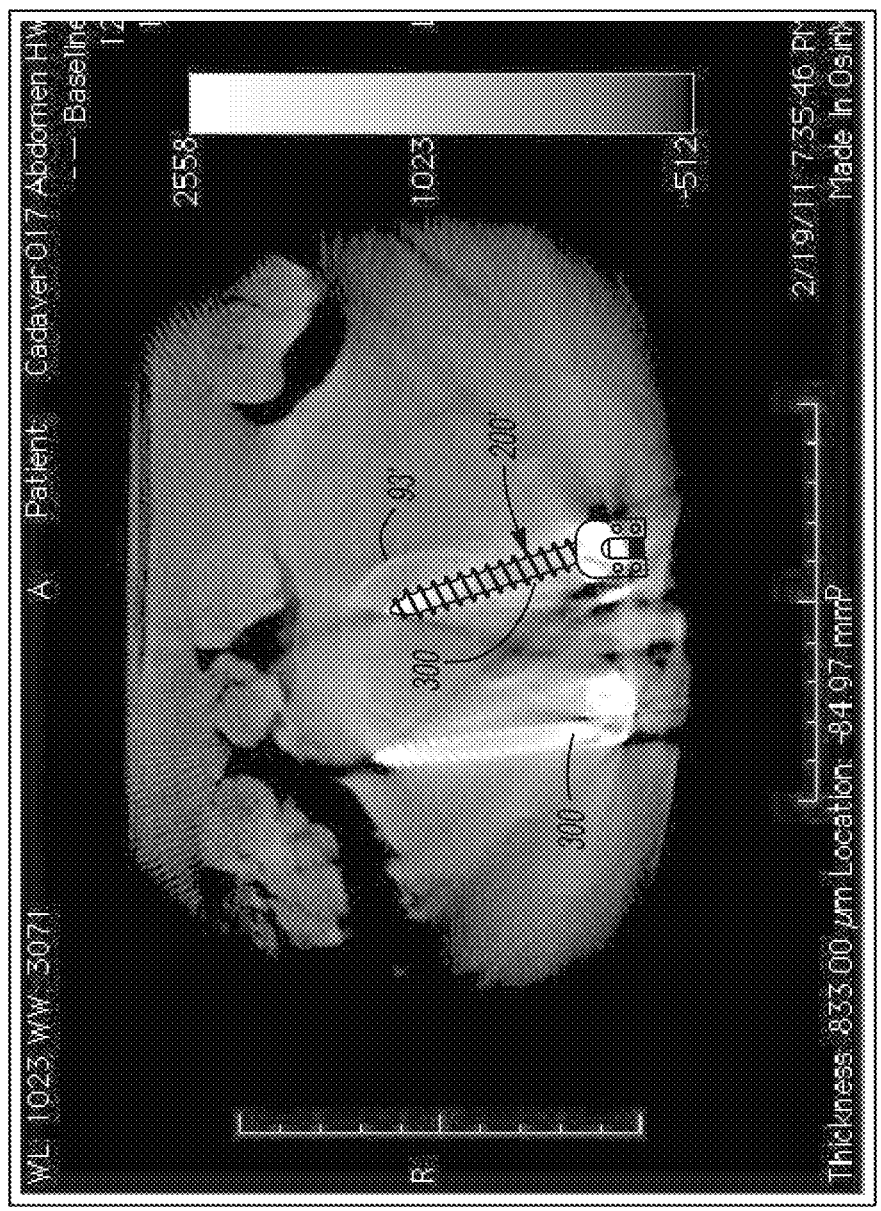
FIG. 6 is a scan image slice illustrating a correction of an artifact caused by an implant according to the present teachings.
Figure 7:
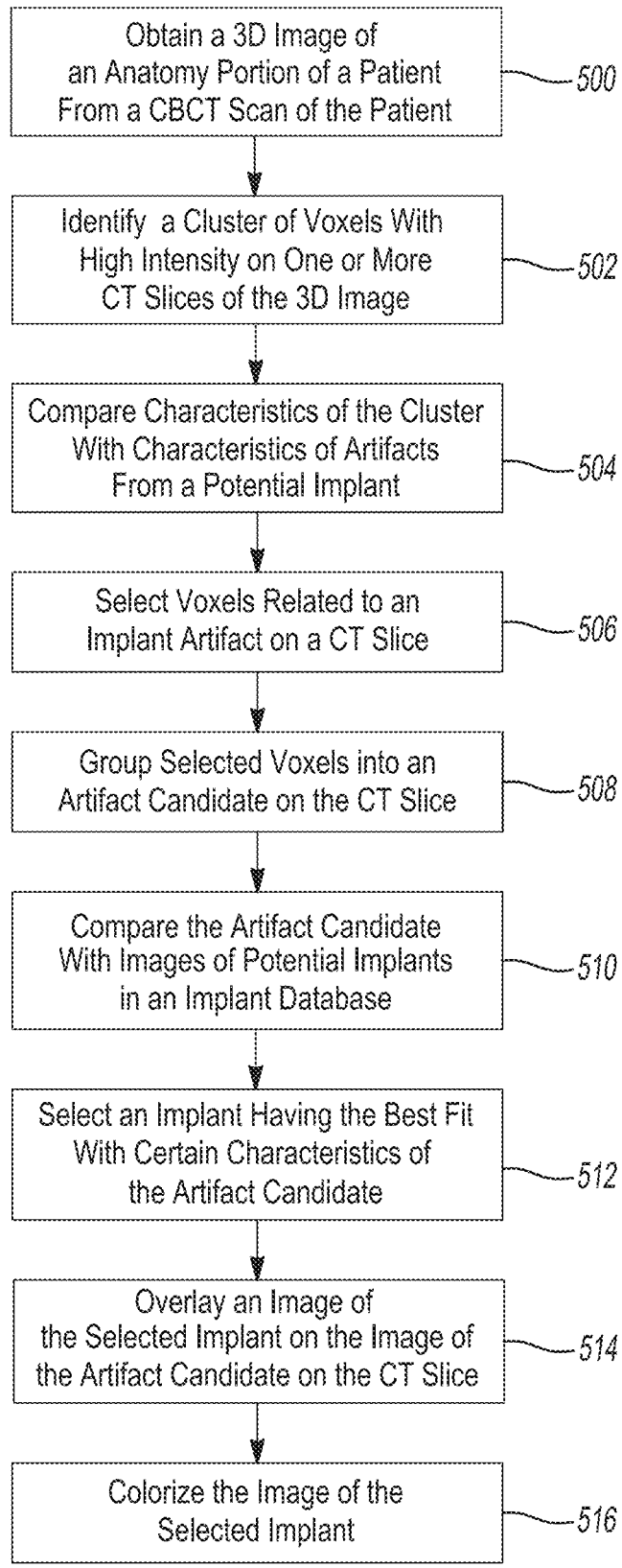
FIG. 7 is a flowchart of an exemplary method according to the present teachings.

Briefly, FIG. 1 illustrates various components of an exemplary CBCT imaging system 10 including x-ray source 36 and a flat panel detector 33. FIG. 2 illustrates a computer system for image processing that can be either part of the imaging system 10, or a separate system that can communicate with a computer or processing modules of the imaging system. FIGS. 3 and 4 illustrate exemplary metal implants associated with the spine. Although the method will be described using spine implants, such as pedicle screws, the present teaching are applicable and encompass to any implants capable of creating x-ray artifacts, including, for example, implants for hip, knee, shoulder, ankle, knee and other joints. The present teaching can also encompass other therapeutic implantable devices, such as cardiac pacing, defibrillation and resynchronization devices, or other implantable devices delivering therapy, including therapy by electrical signals or pulses. FIGS. 5A through 5F illustrate exemplary CT slices showing artifact associated with pedicle screws. FIG. 6 illustrates a CT slice with an image of identified implant overlaid on the artifact image. FIG. 7 is an exemplary flowchart of a method according to the present teachings.

With reference to FIG. 1, a user 12, such as a medical professional, clinician or other assistant, can perform a procedure on a subject, such as a human patient 14. In performing the procedure, the user 12 can use an imaging system 10 to acquire image data of the patient 14 for performing a procedure. The image data acquired of the patient 14 can include two-dimensional (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimensional (3D) volumetric model generated based on the acquired image data using various techniques, including algebraic iterative techniques and generate image data displayable on a display, referenced as displayed image data 18. Displayed image data 18 can be displayed on a display device 20, and additionally, can be displayed on a display device 32*a* associated with an imaging computing system 32. The displayed image data 18 can be a 2D image, a 3D image, or a time changing four-dimensional image. The displayed image data 18 can also include the acquired image data, the generated image data, both, or a merging of both types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22, which can be the same as the image processing computing system 100 shown in FIG. 2. The computing system 22 can include a variety of computer-readable media. The computer-readable media can be any available media that can be accessed by the computing system 22 and can include both volatile and non-volatile media, and removable and non-removable media. The computer-readable media can include, for example, computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, the computing system 22 could be integrated within or be part of the imaging computing system 32 associated with the imaging system 10 or the image processing computing system 100 shown in FIG. 2. A wired or wireless connection 28 can be provided between the computing system 22 and the display device 20 for data communication to allow driving the display device 20 to illustrate the image data 18.

The imaging system 10, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, U.S. Publication No. 2010-0290690, incorporated herein by reference. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

Referring to FIG. 1, the imaging system 10 can include a mobile cart 30 that includes the imaging computing system 32 and an imaging gantry 34 with a source 36, a collimator 37, a flat panel detector 33 (or other type of detector) and a rotor 35. With reference to FIG. 1, the mobile cart 30 can be moved from one operating theater or room to another and the gantry 34 can move relative to the mobile cart 30, as discussed further herein. This allows the imaging system 10 to be mobile so that it can be used in multiple locations and with multiple procedures without requiring a capital expenditure or space dedicated to a fixed imaging system.

With continued reference to FIG. 1, the gantry 34 can define an isocenter of the imaging system 10. In this regard, a centerline Cl through the gantry 34 can define an isocenter or center of the imaging system 10. Generally, the patient 14 can be positioned along the centerline Cl of the gantry 34, so that a longitudinal axis of the patient 14 can be aligned with the isocenter of the imaging system 10.

With reference to FIG. 2, a diagram is provided that illustrates an exemplary embodiment of an image processing computing system 100 which can include the imaging computing system 32 or computing system 22, or can be a separate computing system. The imaging computing system 100 can include a variety of computer-readable media. The computer-readable media can be any available media that can be accessed by the imaging computing system 100 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the image processing computing system 100 comprises a display device 102 and a system unit 104. As illustrated, the display device 104 can comprise a computer video screen or monitor. The image processing computing system 100 can also include at least one input device 106. The system unit 104 can include, as shown in an exploded view, a processor 108 and a memory 110, which can include software with an image processing module (software) 112, an implant database 114 and other data 116, as shown in FIG. 2.

In this example, the at least one input device 106 comprises a keyboard. It should be understood, however, that the at least one input device 106 can comprise any suitable device to enable a user to interface with the image processing computing system 100, such as a touchpad, touch pen, touch screen, keyboard, mouse, joystick, trackball, wireless mouse, audible control or a combination thereof. Furthermore, while the image processing computing system 100 is described and illustrated herein as comprising the system unit 104 with the display device 102, the image processing computing system 100 could comprise a touchpad or tablet computing device or use display device 20.

Briefly, with reference to FIG. 1, the source 36 can emit x-rays through the patient 14 to be detected by the flat panel detector 33. The x-rays can be emitted by the source 36 in a cone beam and can be further shaped by an optional collimator 37 for detection by the flat panel detector 33. An exemplary collimator 37 is commercially available as the Compact Square Field Collimator sold by Collimare Engineering of Wheat Ridge, CO, USA and included with the O-Arm® imaging system sold by Medtronic Navigation, Inc. of Louisville, CO, USA. Briefly, the collimator 37 can include one or more leaves, which can be controlled to shape the x-rays emitted by the source 36. As will be discussed, the collimator 37 can be used to shape the x-rays emitted by the source 36 into a beam that corresponds with the shape of the flat panel detector 33. The source 36, collimator 37 and the flat panel detector 33 can each be coupled to the rotor 35.

Generally, the flat panel detector 33 can be coupled to the rotor 35 so as to be diametrically opposed from the source 36 and the collimator 37 within the gantry 34. The flat panel detector 33 can move rotationally in a 360° motion around the patient 14 generally in the directions of arrow E, and the source 36 and collimator 37 can move in concert with flat panel detector 33 such that the source 36 and collimator 37 remain generally 180° apart from and opposed to the flat panel detector 33.

The gantry 34 can isometrically sway or swing (herein also referred to as iso-sway) generally in the direction of arrow A, relative to the patient 14, which can be placed on a patient support or table 15. The gantry 34 can also tilt relative to the patient 14, as illustrated by arrows B, move longitudinally along the line C relative to the patient 14 and the mobile cart 30, can move up and down generally along the line D relative to the mobile cart 30 and transversely to the patient 14, and move perpendicularly generally in the direction of arrow F relative to the patient 14 to allow for positioning of the source 36, collimator 37 and flat panel detector 33 relative to the patient 14.

The imaging system 10 can be precisely controlled by the image processing computing system 32 to move the source 36, collimator 37 and the flat panel detector 33 relative to the patient 14 to generate precise image data of the patient 14. In addition, the imaging system 10 can be connected with the processor 26 via connection 31 which can include a wired or wireless connection or physical media transfer from the imaging system 10 to the processor 26. Thus, image data collected with the imaging system 10 can also be transferred from the image processing computing system 32 (or 100) to the computing system 22 (or 100) for navigation, display, reconstruction, post-processing etc.

Briefly, with continued reference to FIG. 1, according to various embodiments, the imaging system 10 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. If desired, the components associated with performing a navigated procedure could be integrated within the imaging system 10. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 31, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, a neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 could be graphically illustrated as an icon superimposed on the image data 18.

Further, the imaging system 10 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, the flat panel detector 33, rotor 35, the gantry 34, or other appropriate part of the imaging system 10 to determine the location or position of the source 36, the flat panel detector 33, rotor 35 and/or gantry 34 relative to a selected reference frame. As illustrated, the tracking device 82, 84 can be positioned on the exterior of the housing of the gantry 34. Accordingly, the imaging system 10 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206, filed on May 13, 2009.

In one example, the image data 18 can comprise a single 2D image. In another example, an image control/processing module, such as image processing module 112 (FIG. 2) can perform automatic reconstruction of an initial three dimensional model of the area of interest of the patient 14. Reconstruction of the three dimensional model can be performed in any appropriate manner, such as using algebraic techniques for optimization. Appropriate algebraic techniques include Expectation maximization (EM), Ordered Subsets EM (OS-EM), Simultaneous Algebraic Reconstruction Technique (SART) and total variation minimization. Their application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. In this regard, the stylized model can provide additional detail regarding the anatomy of the patient 14, which can enable the user to plan the surgical intervention much more efficiently. The theoretical model can be associated with theoretical image data to construct the theoretical model. In this way, the model or the image data 18 can be built based upon image data acquired of the patient 14 with the imaging system 10. The image processing module 112 can output image data 18 to the display device 32a or 102.

Referring to FIGS. 3 and 4, an exemplary implant 200 that may cause imaging artifacts in CT scans is illustrated in superior view of a lumbar vertebra 90 (such as L2 vertebra). The vertebra 90 includes a vertebral body 91, a spinous process 94, transverse processes 96, pedicles 92 between the body 91 and the transverse processes 96, and superior articular processes 98. The vertebra has a cortical bone contour 93 surrounding an internal trabecular (cancellous) bone. The cortical bone contour 93, because of it greater density, appears brighter than the spongy trabecular bone on the x-ray images. The implant 200 is a pedicle screw (two pedicle screws 200 are shown in FIG. 3). The pedicle screw 200 includes a head 206 and a threaded shaft 202 having a longitudinal axis A. The pedicle screws 200 are inserted through the pedicle such that their axes are directed toward the apex of the vertebral body 91. The head of the screw 206 is captured by a receiver or seat 204 that is also used for coupling to elongated rods 250 of a spinal fixation system shown in FIG. 4. As shown in FIG. 4, the elongated rods 250 can be secured in the receivers 204 with corresponding locking plugs 208. The heads 206 of the screws are at lower portions of the receivers 204 under the elongated rods 250.

Figure 5A:
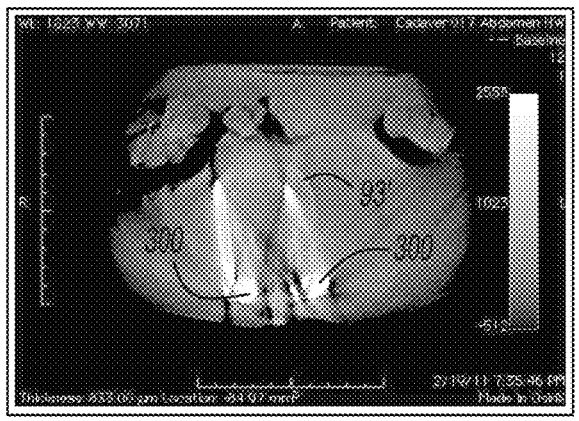
FIG. 5A is a first scan image slice illustrating an artifact caused by an implant.
Figure 5B:
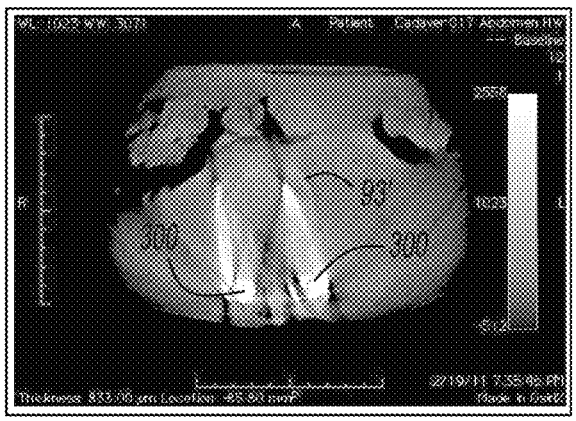
FIG. 5B is a second scan image slice illustrating an artifact caused by the implant of FIG. 5A.
Figure 5C:
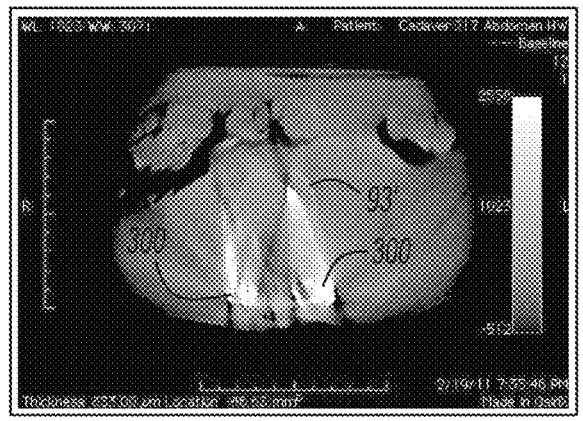
FIG. 5C is a second scan image slice illustrating an artifact caused by the implant of FIG. 5A.
Figure 5D:
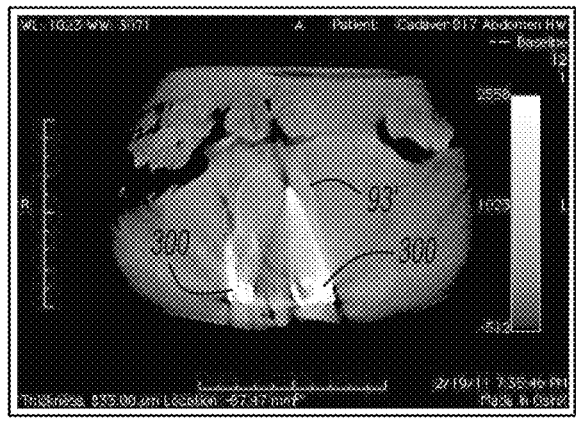
FIG. 5D is a second scan image slice illustrating an artifact caused by the implant of FIG. 5A.
Figure 5E:
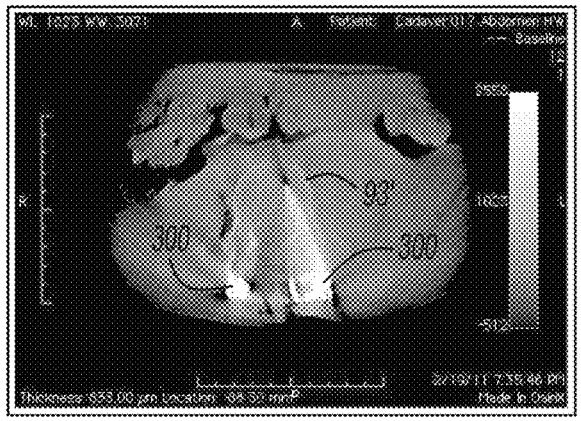
FIG. 5E is a second scan image slice illustrating an artifact caused by the implant of FIG. 5A.
Figure 5F:
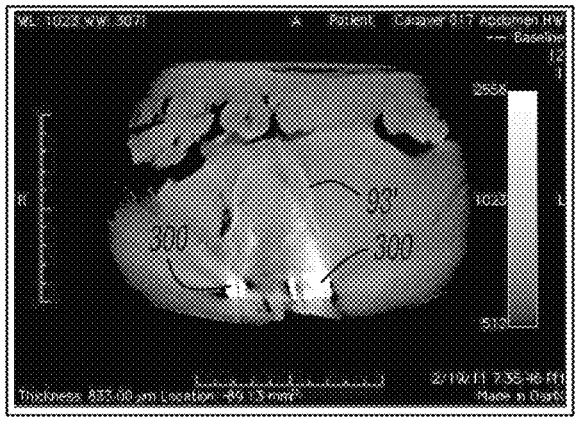
FIG. 5F is a second scan image slice illustrating an artifact caused by the implant of FIG. 5A.

Referring to FIGS. 5A through 5F, images from six CT slices of thickness 833.00 µm at six corresponding locations −84.97 mm, 0.85.40 mm, −86.63 mm, −87.47 mm, −88.30 mm and −89.13 relative to a tagged or reference image (not shown) are illustrated. The images are of a posterior cadaveric spine having two implanted pedicle screws, such as those discussed in connection to FIGS. 3 and 4. In the following description, reference numerals from FIG. 3 are used to describe corresponding elements of the vertebra and pedicle screws in the images of the CT of FIGS. 5A through 5F. In each CT slice, the left and right side of the patient is identified by the letters L and R. To avoid confusion, the left and right sides L and R will be references as radiological left and right (opposite of the left and right sides of the figures). The artifacts 300 around the pedicle screws 200, i.e., areas of increased brightness and "blooming" effects, vary depending of on the location of the CT slices. In some of the CT slices, the image of cortical contour 93' of the vertebral body (shown at 93 in FIG. 3) is obscured, hindering an assessment of whether the pedicle screws 200 are correctly implanted such that their longitudinal axes A are directed toward the apex of the vertebral body 91. For example, the CT slices of FIGS. 5B, 5C, 5D and 5E have the worse artifacts 300 in the sense that the blooming effects become broader and obscure the image of cortical contour 93', making it difficult to determine whether the pedicle screws 200 are correctly positioned. In FIG. 5A, although there is still a lot of artifact 300, the outline or edges of the pedicle screws 200 are visible. In FIG. 5B, the blooming effect is broader, obscuring the cortical contour 93' and making the determination of the direction and location of the left pedicle screw 200 (radiological left marked by L; appears on the right side of FIG. 5B). The blooming effect becomes worse in FIGS. 5C and 5D, and then gradually improves from FIG. 5E to FIG. 5F. Assessing FIGS. 5A and 5F, for example, we can determine that (radiological) right pedicle screw has deviated significantly medially away from the right pedicle 92. Similarly, the (radiological) left pedicle screw 200 appears to be misoriented and very close to spinal canal.

The present teachings provide a method that can identify the particular implant that causes the artifact 300 and overlay a CAD, graphical or other scaled image 200' in outline over the artifact 300, thereby indicating its actual position and orientation, as shown, for example, in FIG. 6. In FIG. 6, the outline of a pedicle screw is overlaid on the radiological left blooming artifact 300, reliably indicating the actual position of the implanted left pedicle screw 200' as well as the shape, size and or type of implanted pedicle screw 200 on the CT slice displayed on a display of computing system, such as display 102 of FIG. 2. An embodiment of the method to position the overlay is briefly outlined in the flowchart of FIG. 7.

As described in reference with FIG. 1, the x-ray source 36 can direct a cone beam of x-rays toward the flat panel detector 36. The subject 14 is positioned such that the region of interest is within the cone beam. By rotating the x-ray source and the detector around the subject 14, a plurality of 2D projections of the region of interest is acquired at block 500 of FIG. 7. The projections can be processed by CBCT reconstruction software to obtain the 3D image of the corresponding anatomy of the subject 14. As discussed above the reconstruction software can be incorporated in the image computing system 32 or computing system 22 or in the image processing system 100, which may separate and communicating systems, overlapping systems or integrated in one system.

Either automatically or by user input, for example, through the input device 106 of FIG. 2, identification of voxels with higher intensity relative to the expected intensity thresholds for bones and tissue of the patient's anatomy is initiated in one or more selected CT slices of the 3D image. A post-processing software module configured to execute image processing commands is incorporated in the image processing module 112 and can identify and locate clusters of voxels that are brighter or have higher contrast than the average brightness of surrounding voxels in a CT slice for the particular range of intensity of the x-ray source 36, at block 502. Isolated voxels of higher than a given threshold intensity may be discarded and adjacent voxels higher than the given threshold intensity may be grouped together for further analysis and identification. To determine whether a cluster of voxels is an artifact of an implant (i.e., an implant candidate), such as a metallic or ceramic screw or other implant, various factors or characteristics of the cluster can be compared with corresponding characteristics of artifacts from a potential implant, at block 504. Characteristics that can be compared include intensity of the image, mass attenuation, density and material composition. These characteristics can be stored in the implant database 114 (FIG. 2), which can include the tables of such properties for common implants for a particular anatomy, such as spinal implants, hip and knee implants or orthopedic and non-orthopedic implants. For example, when a portion of the patient's lumbar spine is imaged, the characteristics of various fixation implants, such as pedicle screws, fixation rods and other implants can be included in the database. In the case of pedicle screws, for example, the database can include the composition, size, shape and orientation relative to vertebral bodies in exemplary spinal fixation or other spinal corrective procedures as well as expected artifact shapes, sizes, brightness, attenuation, density, etc., for comparison. Based on the comparison, voxels potentially related to an implant artifact are selected on a CT slice at block 506 and grouped into an implant candidate (or artifact candidate for an implant) at block 508. At block 510, the implant candidate, i.e., the selected cluster of voxels, can be selected using a best fit analysis and optionally statistical and reliability evaluations of the available data for various characteristics, such as those discussed above. The implant candidate is compared to images and artifacts of potential implants from the implant database 114 at block 510 and a best fit implant is selected from the implant database 114 at block 512. The best fit selection of the implant candidate and corresponding implant can be based on a least square, iterative, weighted or other optimization or probability algorithm. The best-fit algorithm can employ a weighted metric that includes image intensity, mass density, material composition and or other characteristics with corresponding weight factors. The weight factors can be optional or selected based on information available in a database of prior results or other knowledge and experience. The weight factors can be equal, unequal and include zero and nonzero combinations. For example, in some embodiment the image intensity and mass composition can be weighted equally at 50% each, while the mass density is weighted at 0%. In other embodiments, all factors can be weighted equally. The selection of the best fit implant includes, in addition to the inherent characteristics of the selected implant (such as shape, size, type, material composition, etc.), a determination of the orientation and location of the implant relative to the artifact and/or anatomic landmarks on the CT slice. A stylized, CAD, graphical or other image of the selected implant 200' can be overlaid and registered with the determined orientation and location on the CT slice at block 514, as also shown in FIG. 6. The image of the selected implant can be rendered in a selectable color and with a selectable degree of transparency at block 516.

Referring to FIG. 2, the method is performed in an automated manner by the image processing module 112 using the reconstructed 3D image as an input and providing one or more CT slices showing an image of the detected and identified implant overlaid on the CT slices. Optionally, interactive input from a user at an input device 106 can be enabled at the start of the method. Such input can be provided, for example, at blocks 502 to 516 to take advantage of the sometimes superior image recognition performance of the human eye, or verify a selection made by the image processing module 112. Additionally, input regarding the location of CT slices in the 3D image can be provided as an input by the user.

Figure 8:
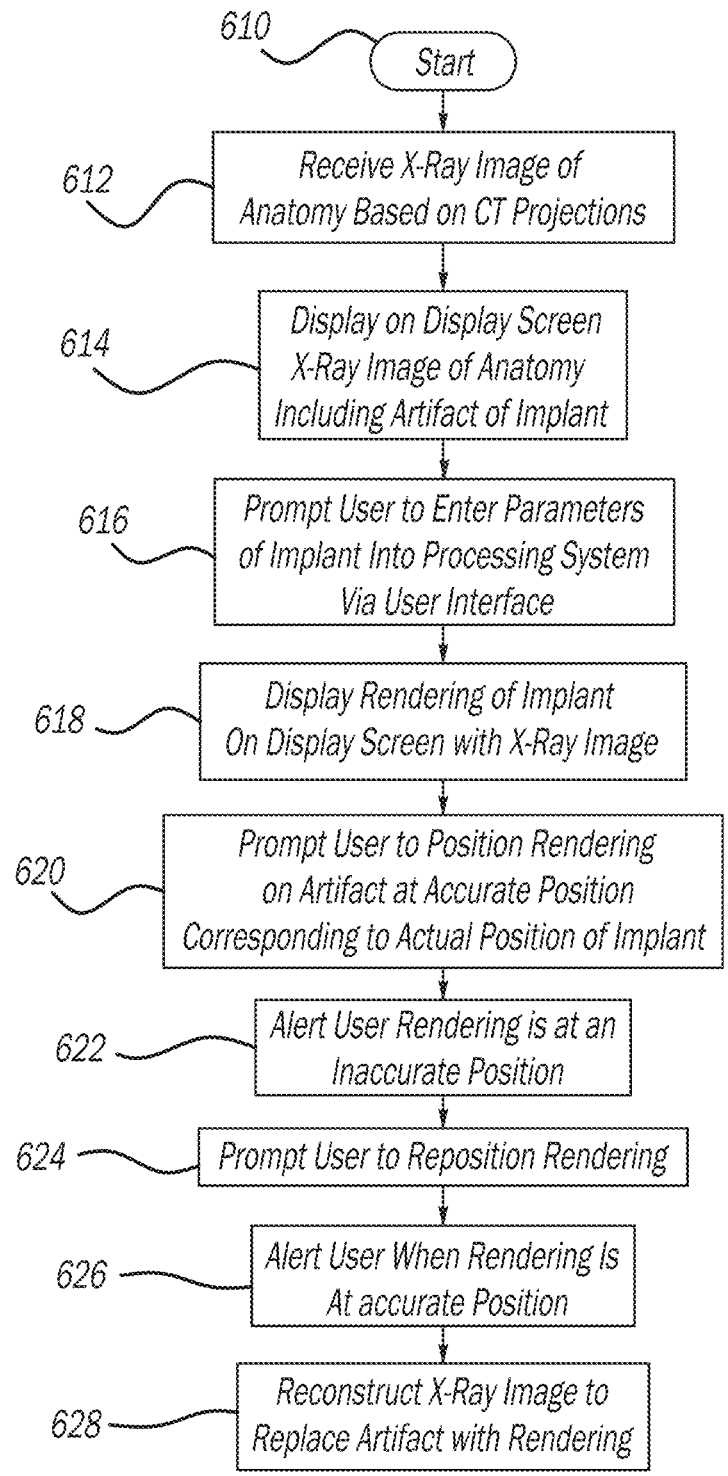
FIG. 8 is a flowchart of an additional exemplary method according to the present teachings.
Figure 9:
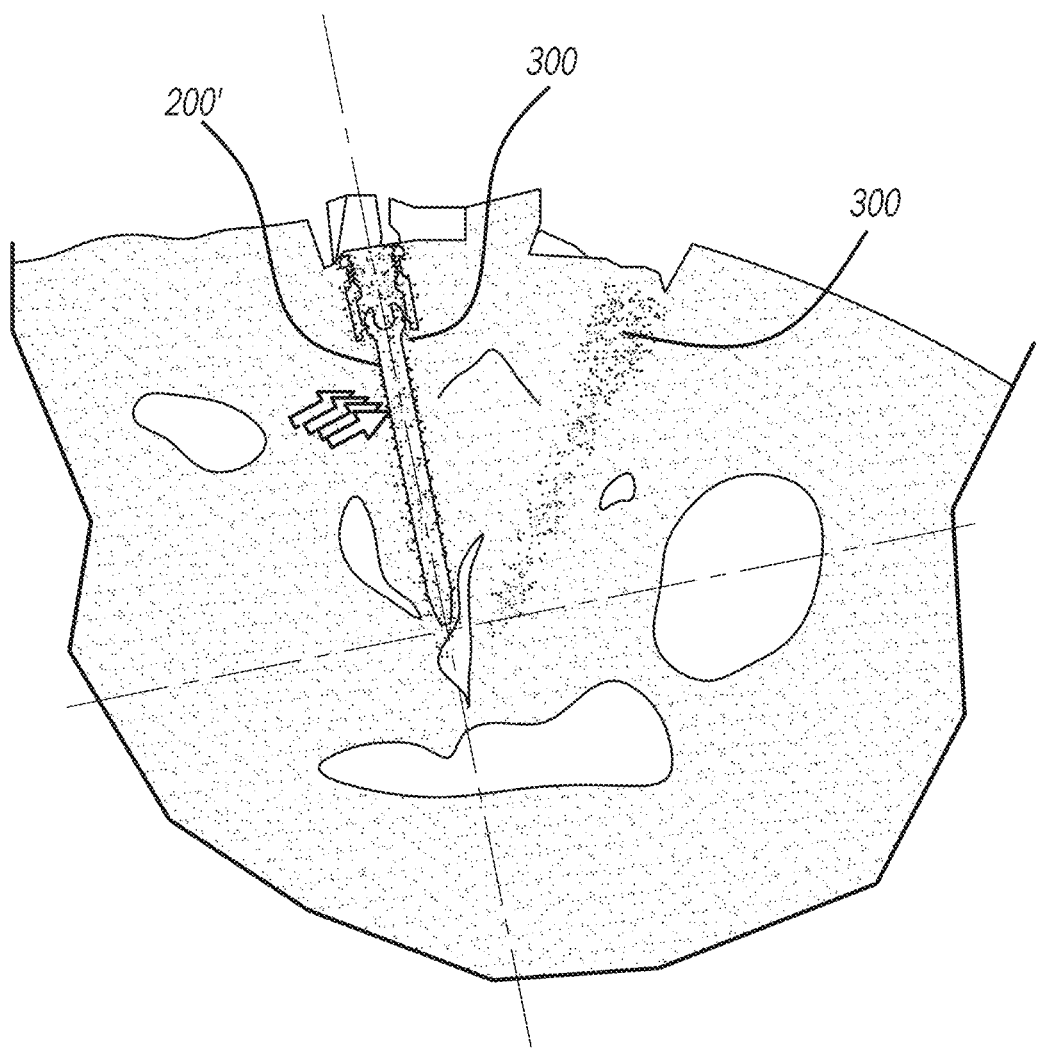
FIG. 9 is a scan image slice illustrating artifacts caused by scanning implants, and an implant rendering that is movable in the image by a user.

FIG. 8 generally illustrates an additional method in accordance with the present disclosure for identifying an implant in an x-ray image of an anatomy shown on a display screen. The method generally starts at block 610, where an x-ray image of the anatomy is received by the image processing computing system 100 of FIG. 2. The x-ray image is a 3D image reconstructed from the 2D projections taken with the imaging system 10. At block 614, the x-ray image is displayed, such as on the display 102 of the image processing computing system 100. The x-ray image includes one or more implants in the imaged anatomy, such as spinal screws (which may include a tulip head), for example. Any other suitable implant may be imaged as well. For at least the reasons set forth above, the implants are obscured in the image by artifacts 300, and thus the exact position of the implants cannot be clearly seen in the x-ray image. FIG. 9 illustrates an exemplary x-ray image with artifacts 300 obscuring implanted spinal screws.

At block 616, the system 100 prompts a user to enter parameters of the implants by way of any suitable user interface, such as the input device 106. Any suitable parameters may be entered, such as, but not limited to, the following: implant system, implant set, implant type, implant diameter, and implant length. At block 618, the system 100 selects a rendering of an implant from the implant database 114 that matches the implant parameters entered by the user. For example, if the implant parameters match the implant 200, the system 100 displays on the display 102 a rendering 200'. The rendering 200' is displayed on the x-ray image over the anatomy (see FIG. 9). The rendering 200' is sized and shaped to correspond to the entered parameters of the implant. Using the input device 106, or any suitable input device, the user is able to move the rendering 200' about the x-ray image, as illustrated in FIG. 9, for example. At block 620, the system 100 prompts the user to position the rendering on the artifact 300 at an accurate position corresponding to an actual position where the user believes the actual implant 200 is or should be.

At block 622, the system 100 compares the position of the rendering 200' to an actual position of the implant 200. If the rendering 200' is at an inaccurate position that is outside of a predetermined distance from the accurate position, the system 100 generates a notification to the user. And at block 624, the system 100 prompts the user to reposition the rendering 200' to an accurate position. The predetermined distance from the accurate position may be any suitable distance. With respect to a spinal screw, for example, the predetermined distance may be +/−2 mm for a rendered screw tip from the actual position of the implanted screw tip, and +/−10° for a rendered screw head from the actual position of the implanted screw head. With the rendered position at block 620, the pre-check algorithm will check whether there is an actual implant existing on the x-ray image of the anatomy within certain region of the rendered position. This is done by comparing the volume ROI with the images of selected implant in the implant database. The system 100 will continue to prompt the user to reposition the rendering at block 624 until the user positions the rendering 200' within the predetermined distance from the accurate position of the implant. Once the user positions the rendering 200' at the accurate position corresponding to the actual position of the implant 200, the system 100 generates an alert notifying the user that the rendering 200' is properly positioned.

Figure 10:
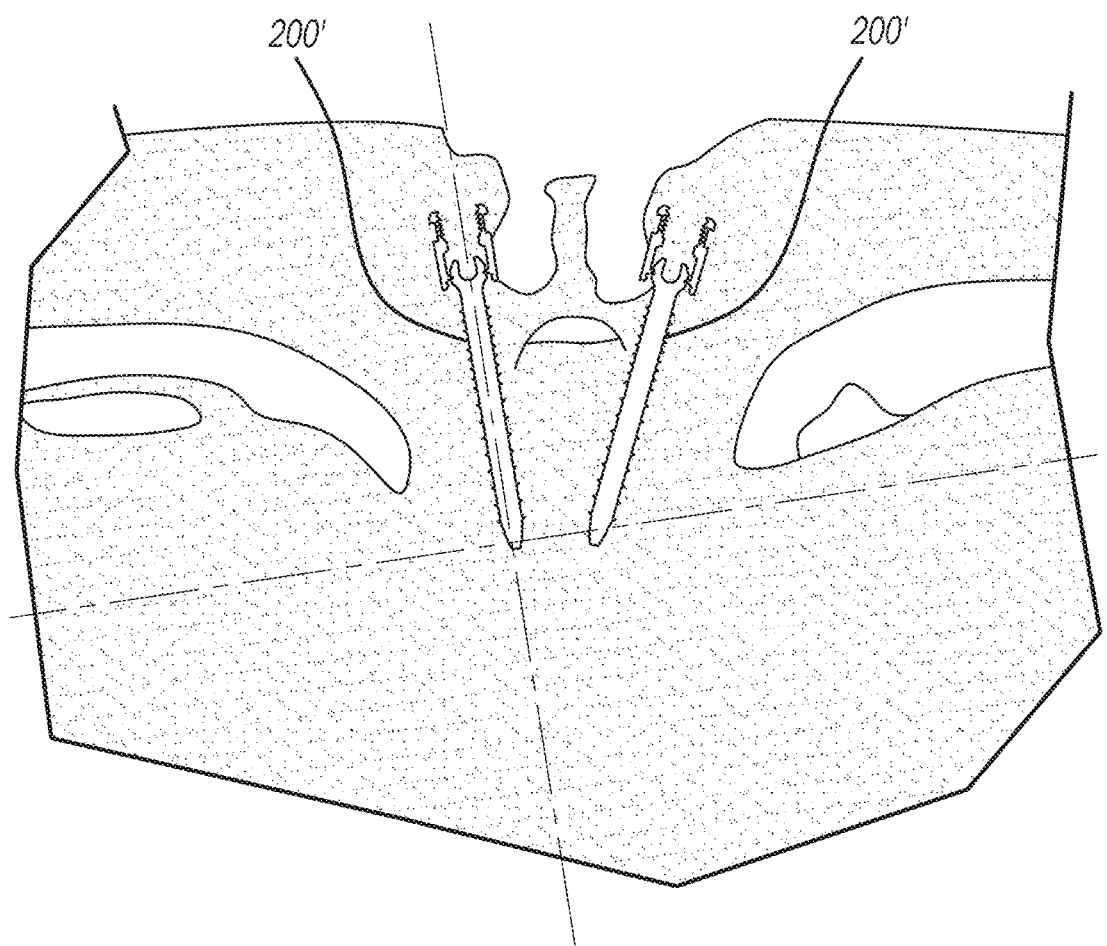
FIG. 10 is a scan image slice illustrating replacement of the artifacts of FIG. 10 with implant renderings.

After the rendering 200' has been accurately positioned on the x-ray image by the user, at block 628 the system 100 reconstructs the x-ray image to replace the artifact 300 with the rendering 200' affixed in the accurate position. FIG. 10 illustrates an exemplary x-ray image where two of the artifacts 300 have each been replaced with an affixed rendering 200' positioned by the user. The system 100 may be configured to allow the user to position each rendering 200' one at a time. After the user successfully positions one of the renderings 200' at an accurate position, the system 100 will begin to reconstruct the x-ray image to replace the corresponding artifact with the affixed rendering 200'. As the system 100 is reconstructing the image, the user and system 100 may repeat at least the steps at blocks 616-626 to position another rendering 200' for an additional implant 200, and then at block 628 an additional reconstruction of the x-ray image is performed for the additional implant 200.

Additional advantages of the present disclosure include the following: (1) the user can choose which implants in the x-ray image need artifact correction for clinical purposes, as opposed to automated positioning, which automatically applies artifact correction on all implants presented on the x-ray volume; (2) avoids ambiguity on the implant selection; and (3) the pre-check mechanism (block 622) ensures the implant with artifact reduction is placed within the specified tolerance.

The present teachings provide a computer-implemented method for identifying and displaying implants from artifacts in CT slices of a 3D image of a patient's anatomy. The 3D image can be reconstructed from 2D projections of a CT or CBCT imaging system, such as, for example, the imaging system 10, in a processor (such as processor 108 of FIG. 2) of a computing system associated with the imaging system, such as, for example, the computing system 32 or 22 shown in FIG. 1 or the computing system 100 shown in FIG. 2. While the 3D image reconstruction can be performed during the imaging session (intraoperatively), the identification of implants causing artifacts is a post-processing procedure performed using axial sections or CT slices. The processor 108 compares the intensity and contrast characteristics of voxels in the 3D image and various CT slice locations and selects clusters of voxels with characteristics associated with known implant artifacts. The characteristics of each identified cluster of voxels are compared with similar characteristics of artifacts of known implants in an implant database, such as implant database 114 in FIG. 2. Least square or other optimization and reliability algorithms can be used to select the best fit implant for a selected artifact that is an implant candidate. An image of the identified implant can be registered and overlaid in the scale of the CT slice on the image of the CT slice in the display 102 of the image processing computing system 100. The image of the implant can be a wire or solid CAD drawing or other digital rendering of the implant and include colorization of a contour of the image or filler colorization of the image of the implant with selected degrees of transparency, contrast and shades of color to enhance recognition and identification of the image of the implant on the CT slice.

Summarizing, the present teachings provide a method of detecting an identifying an implant in a CT slice of a reconstructed 3D image of a patient's anatomy. The method analyzes and identifies voxels associated with image artifacts and compares clusters of selected voxels with artifact characteristics associated with implants in an implant database. A best fit implant is determined and an image of the best fit implant is registered and overlaid on the CT slice and viewed on a display of an image processing computing system. This information enables the user to better asses and evaluate the condition of recent or old therapy or procedure and plan a corrective or new procedure taking into account the location and orientation of the implant and its characteristics.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A method for identifying an implant in an image of an anatomy shown on a display screen, the method comprising:
receiving, in a processing system, computed tomography (CT) slices of the anatomy;
displaying the image of the anatomy on the display screen based on the CT slices, the image including an artifact portions due to the implant;
prompting a user to enter parameters of the implant into the processing system by way of a user interface;
displaying a rendering of the implant on the display screen along with the image, the rendering sized and shaped to correspond to the implant;
prompting the user to position the rendering of the implant at an accurate position on the artifact portions corresponding to an actual position of the implant in the anatomy that includes portions of the artifact portions; and
at least one of:
alerting the user when the rendering is positioned by the user at an inaccurate position relative to the artifact portions that is outside of a predetermined distance from the accurate position, and
prompting the user to reposition the rendering from the inaccurate position; or
alerting the user when the rendering is positioned by the user to the accurate position including within the predetermined distance of the accurate position, and
after the rendering has been positioned to the accurate position by the user, reconstructing the image to replace the artifact portions with the rendering in the accurate position;
wherein the predetermined distance is +/−2 mm for a rendered screw top from a screw tip of the implant, and +/−10° for a rendered screw head from a screw head of the implant.

2. The method of claim 1, wherein the implant is a spinal screw.

3. The method of claim 1, wherein the implant is a spinal screw including a tulip head.

4. The method of claim 1, wherein the parameters of the implant include at least one of implant system, implant set, implant type, implant diameter, and implant length.

5. The method of claim 1, further comprising prompting the user to enter parameters of additional implants, and prompting the user to position additional renderings of the additional implants during the reconstructing of the image.

6. The method of claim 1, further comprising prompting the user to toggle between the reconstructed image and the image including the artifact portions.

7. The method of claim 1, wherein the implant is a spinal screw configured to mount a spinal rod; and
wherein the method is performed after the spinal screw has been implanted, and before the spinal rod has been mounted to the spinal screw.

8. The method of claim 1, wherein the rendering of the implant is three-dimensional.

9. An image processing system for identifying an implant in an image of an anatomy shown on a display screen, the system comprising:
a computing system including a processor and a memory storage and an image processing software module, an implant database accessible by the processor, a display, and an input device, wherein the processor is configured to:
prompt a user to enter parameters of the implant to the processor by way of the input device;
select a rendering of the implant from a database saved in the memory storage;
display the rendering of the implant on the display along with the image, the rendering of the implant sized and shaped to correspond to the implant;
prompt the user to position the rendering of the implant on artifact portions in the image at an accurate position corresponding to an actual position of the implant in the anatomy;
at least one of:
alert the user when the rendering of the implant is positioned by the user to an inaccurate position that is outside of a predetermined distance from the accurate position, and
prompt the user to reposition the rendering of the implant from the inaccurate position to the accurate position, or alert the user when the rendering of the implant is positioned by the user to the accurate position, or within the predetermined distance of the accurate position; and reconstruct the image to replace the artifact portions with the rendering of the implant in the accurate position after the rendering of the implant has been positioned at the accurate position by the user;

wherein the predetermined distance is +/−2 mm for a rendered screw tip from a screw tip of the implant, and +/−10° for a rendered screw head from crew d of the implant.

10. The system of claim 9, wherein the implant is a spinal screw.

11. The system of claim 9, wherein the implant is a spinal screw including a tulip head.

12. The system of claim 9, wherein the parameters of the implant include at least one of implant system, implant set, implant type, implant diameter, and implant length.

13. The system of claim 9, further comprising prompting the user to enter parameters of additional implants, and prompting the user to position additional renderings of the additional implants during the reconstructing of the image.

14. The system of claim 9, further comprising prompting the user to toggle between the reconstructed image and an original image including the artifact.

15. The system of claim 9, wherein the rendering of the implant is three-dimensional.

* * * * *